US009743965B2

(12) United States Patent
Kobayashi et al.

(10) Patent No.: US 9,743,965 B2
(45) Date of Patent: Aug. 29, 2017

(54) MEDIAL COLUMN FUSION PLATES

(71) Applicant: DePuy Synthes Products, LLC, Raynham, MA (US)

(72) Inventors: Kenneth I. Kobayashi, West Chester, PA (US); Mark Siravo, East Norristown, PA (US); Rene Haag, West Chester, PA (US); Sherri Wykosky, Media, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 383 days.

(21) Appl. No.: 14/310,265

(22) Filed: Jun. 20, 2014

(65) Prior Publication Data
US 2015/0366597 A1  Dec. 24, 2015

(51) Int. Cl.
*A61B 17/80* (2006.01)
(52) U.S. Cl.
CPC .......... *A61B 17/8061* (2013.01); *A61B 17/80* (2013.01); *A61B 17/8004* (2013.01);
(Continued)
(58) Field of Classification Search
CPC . A61B 17/80; A61B 17/8004; A61B 17/8019; A61B 17/8052; A61B 17/8057; A61B 17/8061; A61B 17/8085
See application file for complete search history.

(56) References Cited

U.S. PATENT DOCUMENTS 7,905,910 B2  3/2011 Gerlach et al.
8,246,664 B2 * 8/2012 Terrill ................ A61B 17/8061
606/280
(Continued)

FOREIGN PATENT DOCUMENTS

DE  202007002190 U1  4/2007
DE  202009006648 U1  8/2009
(Continued)

*Primary Examiner* — Larry E Waggle, Jr.
(74) *Attorney, Agent, or Firm* — Fay Kaplun & Marcin, LLP (57) ABSTRACT

A medial column bone plate, comprises a first portion which, when the plate is positioned along a medial column of a foot in a desired position, extends along a navicular, the first portion including at least two first variable angle holes extending therethrough, each of the first variable angle holes configured to receive a bone fixation element therethrough at a user-selected angle relative to a central axis thereof and a second portion extending distally from the first portion so that when the plate is in the desired position, the second portion extends along a medial cuneiform, the second portion including at least one second variable angle hole configured to receive a bone fixation element therein at a user-selected angle relative to a central axis thereof and a first compression slot extending therethrough in combination with a third portion extending distally from the second portion so that the third portion extends along a first metatarsal of the medial column in the desired position, the third portion including a third variable angle hole configured to receive a bone fixation element therein at a user-selected angle relative to a central axis thereof and a second compression slot extending therethrough.

18 Claims, 6 Drawing Sheets (52) U.S. Cl.
CPC ...... *A61B 17/8019* (2013.01); *A61B 17/8052* (2013.01); *A61B 17/8057* (2013.01); *A61B 17/8085* (2013.01)

(56) References Cited

U.S. PATENT DOCUMENTS

| | | | |
|---|---|---|---|
| 8,257,403 | B2 | 9/2012 | Den Hartog et al. |
| 8,936,615 | B2 * | 1/2015 | Pappalardo ........ A61B 17/8019 606/105 |
| 2011/0092981 | A1 * | 4/2011 | Ng .................... A61B 17/1728 606/101 |
| 2011/0264149 | A1 | 10/2011 | Pappalardo et al. |
| 2013/0172942 | A1 | 7/2013 | Lewis et al. |
| 2014/0012328 | A1 | 1/2014 | Prasad et al. |

FOREIGN PATENT DOCUMENTS

| | | |
|---|---|---|
| DE | 202009008872 | 9/2009 |
| DE | 202008012448 U1 | 4/2010 |
| DE | 102009020285 | 11/2010 |
| DE | 202011051165 U1 | 11/2011 |
| EP | 1 616 528 | 1/2006 |
| EP | 1 897 509 | 12/2008 |

\* cited by examiner

MEDIAL COLUMN FUSION PLATES

BACKGROUND

Conditions such as Charcot foot and severe arthritis may weaken bones and/or cause joints to collapse. The weakening of bone and/or the collapse of the joints may eventually result in foot deformities such as an unstable medial column. These conditions may make it extremely difficult to walk. In some cases, foot deformities may be treated using bone plates designed to fix bones of the foot (e.g., bones of the medial column) relative to one another.

SUMMARY OF THE INVENTION

The present invention is directed to a medial column bone plate, comprising a first portion which, when the plate is positioned along a medial column of a foot in a desired position, extends along a navicular, the first portion including at least two first variable angle holes extending therethrough, each of the first variable angle holes configured to receive a bone fixation element therethrough at a user-selected angle relative to a central axis thereof and a second portion extending distally from the first portion so that when the plate is in the desired position, the second portion extends along a medial cuneiform, the second portion including at least one second variable angle hole configured to receive a bone fixation element therein at a user-selected angle relative to a central axis thereof and a first compression slot extending therethrough in combination with a third portion extending distally from the second portion so that the third portion extends along a first metatarsal of the medial column in the desired position, the third portion including a third variable angle hole configured to receive a bone fixation element therein at a user-selected angle relative to a central axis thereof and a second compression slot extending therethrough.

DETAILED DESCRIPTION

The present invention may be further understood with reference to the following description and the appended drawings, wherein like elements are referred to with the same reference numerals. The present invention is directed to a plate for treating foot deformities and, in particular, relates to bone plates providing fusion of joints to stabilize the medial column. Exemplary embodiments of the present invention describe a bone plate including a plurality of variable angle holes along with a plurality of compression holes positioned along the plate to provide independent compression of the joints of the medial column. It will be noted that the plates described and shown in the exemplary embodiments may be specifically configured for application to either the left foot or the right foot of a patient. In particular, plates designed for left and right foot configurations may be mirror images of one another. It should also be noted that, as would be understood by those skilled in the art, although the exemplary embodiments describe the use of compression wires, compression posts, compression pins, bone fixation elements or other suitable elements may also be inserted through compression slots of the plates to provide compression to the joints of the medial column. Furthermore, as would be understood by those skilled in the art, any of the variable angle holes described may be replaced by a fixed angle locking hole or a non-locking hole as desired.

Figure 1:
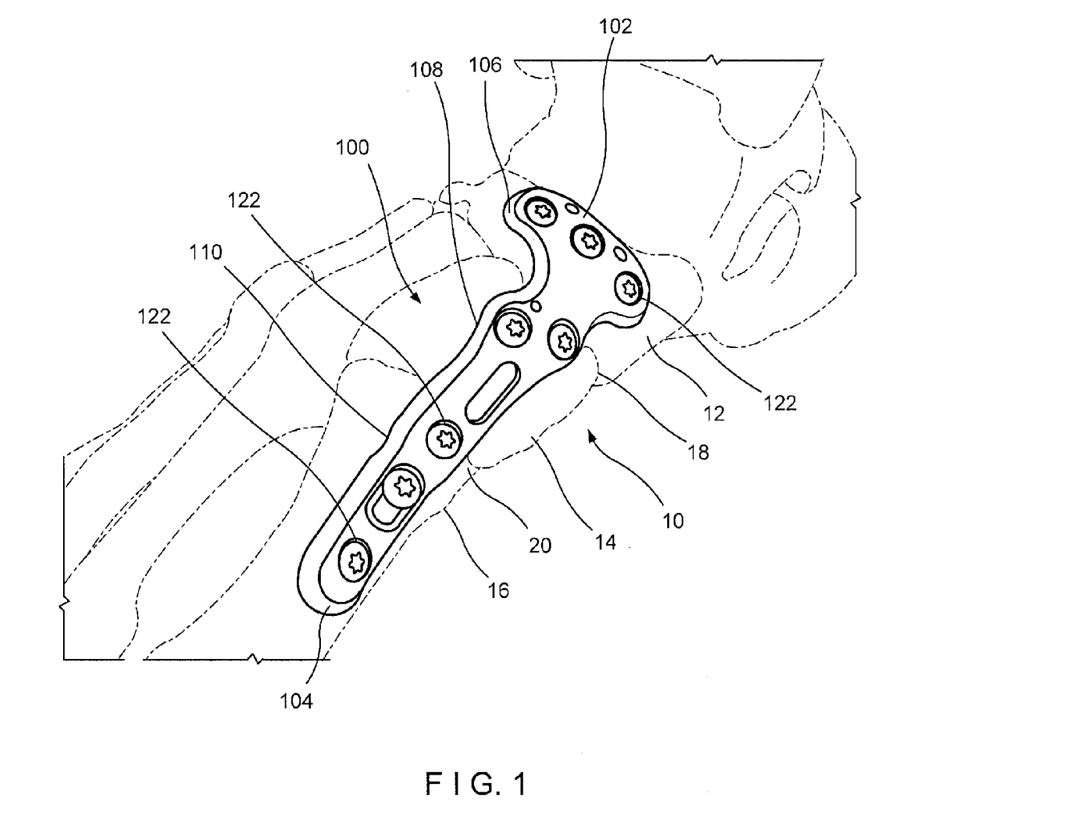
FIG. 1 shows a perspective view of a bone plate according to a first exemplary embodiment of the present invention.
Figure 2:
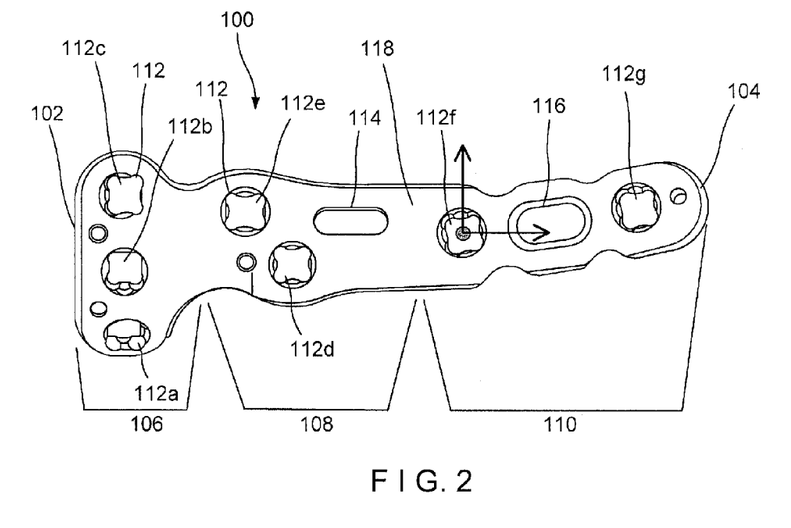
FIG. 2 shows a top plan view of the bone plate of FIG. 1.
Figure 3:
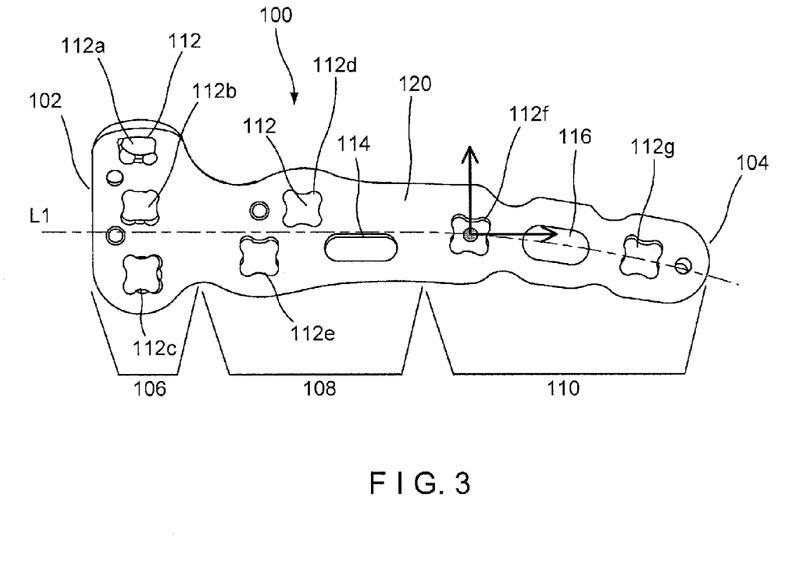
FIG. 3 shows a bottom plan view of the bone plate of FIG. 1.

As shown in FIGS. 1-3, a bone plate 100 according to an exemplary embodiment of the present invention extends along a longitudinal axis L1 from a proximal end 102 to a distal end 104 and, in particular, is configured to extend along a medial column 10 of a foot of a patient. In one exemplary embodiment, a length of the plate 100 is designed to span a navicular 12, medial cuneiform 14 and a first metatarsal 16 of the medial column 10 of a patient. The plate 100 includes a first portion 106 which, when the plate 100 is placed in a desired position along the medial column 10, extends along the navicular 12, a second portion 108 which extends along the medial cuneiform 14 in the desired position, and a third portion 110 which extends along the first metatarsal 16. The bone plate 100 further comprises a plurality of openings 112 extending therethrough from a first surface 118 which, when the plate 100 is in a desired position along the medial column 10, faces away from the medial column 10, to a second surface 120 which faces the medial column 10 in the desired position. Each of the openings 112 extends through the plate 100 from the first surface 118 to the second surface along a central axis. Each of the openings 112 is sized and shaped to receive a bone fixation element 122 for fixing a portion of the plate 106, 108, 110 to a corresponding one of the bones 12, 14, 16. Each of the openings 112 may, for example, be a variable angle hole. As understood by those skilled in the art, a variable angle hole is configured to receive a bone fixation element 122 therein at any user-selected angle (relative to a central axis of the hole) within a permitted range of angulations. The plate 100 further comprises a first compression slot 114 extending through the second portion 108 and a second compression slot 116 extending though the third portion 110 of the plate 100. The first and second compression slots 114, 116 are positioned along the plate 100 relative to the openings 112 to permit independent compression of a first naviculocuneiform joint 18 and a tarsometatarsal joint 20 of the medial column 10, respectively.

The first portion 106 of the plate 100 has a width (e.g., a distance between longitudinal edges of the plate 100 farthest from the longitudinal axis L1) larger than a width of a remaining portion of the plate permitting the first portion 106 to include a plurality of openings 112 to be placed therein side-by-side (i.e., in a direction transverse to the longitudinal axis L1). In one exemplary embodiment, the first portion 106 includes three openings 112a, 112b, 112c, separated from one another along an axis substantially perpendicular to the longitudinal axis L1. The first portion 106 in this embodiment is pre-contoured to substantially correspond to a shape of a surface of the navicular 12 over which it is to be mounted. Those skilled in the art will understand that a user may further contour the any portion of the plate as desired to tailor the plate to the anatomy of a patient.

As described above, the second portion 108 extends distally from the first portion 106 so that, in the desired position, it extends over a portion of the medial cuneiform 14. In one exemplary embodiment, the cuneiform portion 108 includes two openings 112d, 112e extending through a proximal portion thereof, each of the openings 112 offset from one another along the length of the plate 100 and offset from each other relative to the longitudinal axis L1. In particular, a first one 112d of the openings 112 may be positioned slightly distally of a second one 112e of the openings 112 on a first side of the longitudinal axis L1, while the second one 112e of the openings 112 is positioned on a second side of the longitudinal axis L1 opposing the first side. The first compression slot 114 is formed in the second portion 108 distally of the openings 112d, 112e extending therethrough from the first surface 118 to the second surface 120. The compression slot 114 is elongated along an axis substantially parallel to the longitudinal axis L1 and is sized to receive a compression wire, post, pin and/or bone fixation element therein such that the first naviculocuneiform joint 18 may be compressed using, for example, forceps configured to engage a portion of the wire, post, pin and/or fixation element.

As described above, the third portion 110 extends distally from the first portion 108 to extend over a portion of the first metatarsal 16, in the desired position. The third portion 110 in this embodiment includes a first opening 112f through a proximal portion of the third portion 110 and a second opening 112g distal to the first opening 112f. The second compression slot 116 is located between the openings 112f, 112g and extends through the third portion from the first surface 118 to the second surface 120 thereof The second compression slot 116 is elongated along the longitudinal axis L1 and is sized to receive a compression wire, post, pin, screw or other bone fixation element therein and, in this embodiment, extends along a curve in a plane extending through the longitudinal axis L1 and substantially perpendicular to a central axis of the opening 112f. The curve of the third portion 110 in this embodiment substantially corresponds to a natural curvature of the first metatarsal 16 relative to the navicular 12 and medial cuneiform.

As described above, the first and second compression slots 114, 116 are separated from one another along a length of the plate 100 via openings 112 to provide independent compression of the naviculocuneiform and tarsometatarsal joints 18, 20.

According to an exemplary surgical method using the plate 100, a surgeon or other user makes an incision in the skin over the medial column 10 of the foot. The joints 18, 20 may be prepared for fusion by substantially aligning the bones along a tarsometatarsal axis and/or correcting any deformities with bone resections or bone grafts. The plate 100 is preferably pre-contoured to substantially correspond to a shape of an exterior surface of the bones of the medial column 10 over which it is to be mounted. The bone plate 100 may be further contoured to accommodate specific patient anatomy and provide a desired correction of the medial arch as would be understood by those skilled in the art. The plate 100 is then be positioned along the medial column 10 with the first portion 106 extending over the navicular 12, the second portion 108 extending over the medial cuneiform 14, and the third portion 110 extending over the first metatarsal 16. Once the plate 100 has been positioned, as desired, a bone fixation element 122 (e.g., a variable angle locking screw) may be inserted through one of the openings of the first portion 106 of the plate 100, into the navicular 12. In particular, the bone fixation element 122 may be inserted into the opening 112a, closest to a lateral side of the patient's foot. A first compression wire or post is then inserted into one of the remaining openings 112b, 112c of the first portion 106 while a second compression wire or post is inserted into the first compression slot 114. The second compression wire or post is inserted into a distal end of the first compression slot 114 so that compression forceps, or any other suitable compression device, may be employed to compress the first naviculocuneiform joint 18 via the first and second compression wires or posts. Once the first naviculocuneiform joint 18 has been compressed as desired, a bone fixation element 122 is inserted through one of the openings 112d, 112e of the second portion 108 to fix the plate 100 in position to maintain the desired compression.

Leaving the first compression wire or post in place, the second compression wire is removed from the first compression slot 114 and a third compression wire or post is inserted into the second compression slot 116. Similarly to the compression wire in the first compression slot 114, the third compression wire or post may be inserted at a distal end of the second compression slot 116 to maximize a potential compression. Using the compression forceps, compression is then applied to the tarsometatarsal joint 20. Once the tarsometatarsal joint 20 has been compressed as desired, a bone fixation element 122 is inserted through one of the openings 112f, 112g of the third portion 110. Additional bone fixation elements 122 may be inserted into any of the remaining openings 112, 116 to further fix the plate 100 to the bones of the medial column 10.

Figure 4:
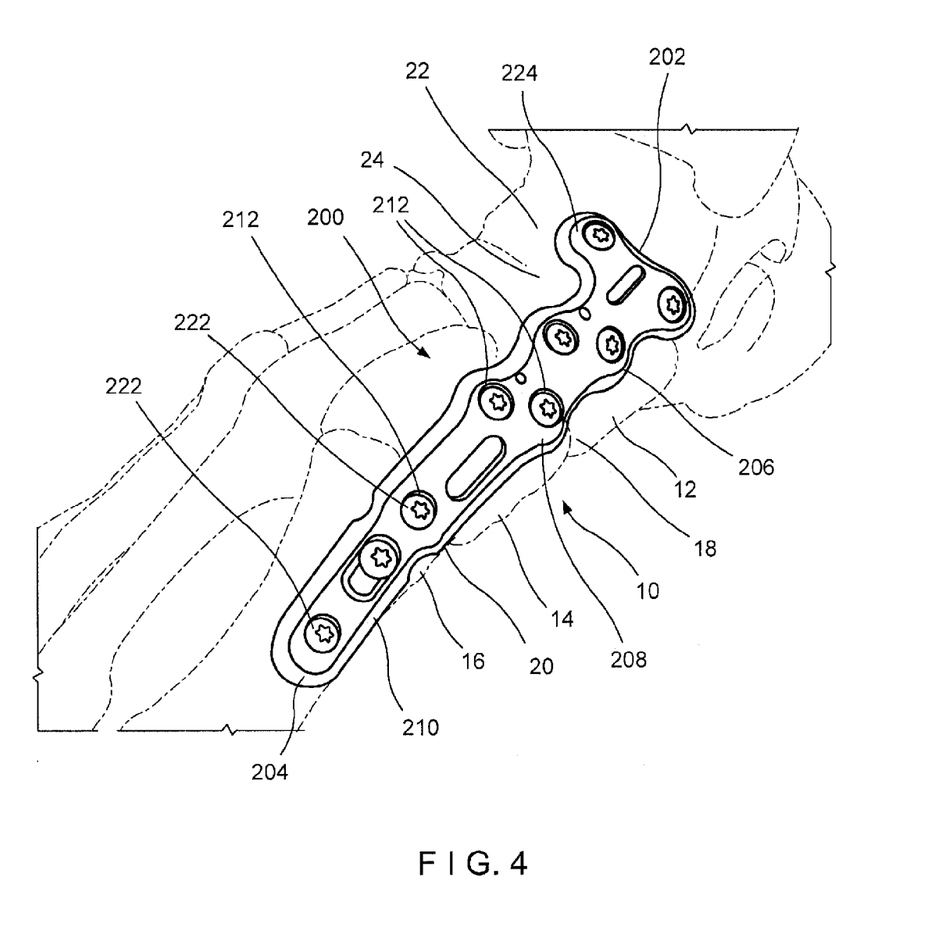
FIG. 4 shows a perspective view of a bone plate according to a second exemplary embodiment of the present invention.
Figure 5:
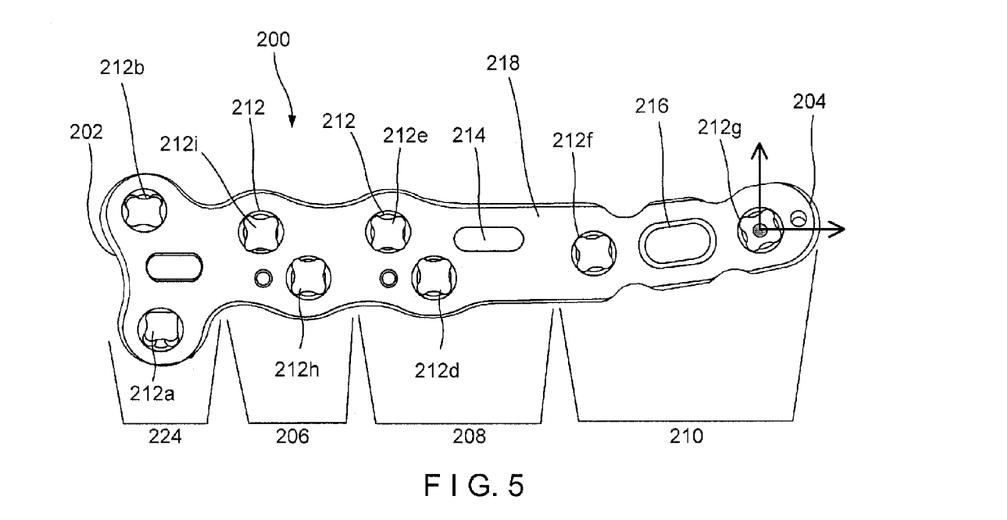
FIG. 5 shows a top plan view of the bone plate of FIG. 4.
Figure 6:
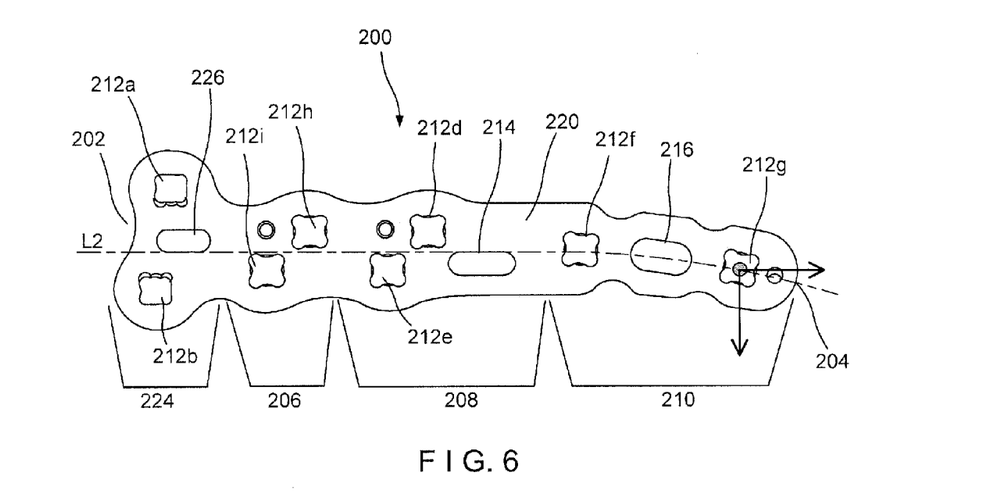
FIG. 6 shows a bottom plan view of the bone plate of FIG. 4.

As shown in FIGS. 4-6, a bone plate 200 is substantially similar to the bone plate 100 extending longitudinally from a proximal end 202 to a distal end 204 and is structured so that, when the plate 200 is placed along the medial column 10 in a desired position, a first portion 206 extends along the navicular 12, a second portion 208 which extends along the medial cuneiform 14 and a third portion 210 extends along the first metatarsal 16. Similarly to the plate 100, the plate 200 includes a plurality of openings 212 extending therethrough from a first surface 218 which, when the plate 200 is in the desired position faces away from the medial column 10, to a second surface 220 which faces the medial column 10. As described above in regard to the plate 100, any or all of the openings 212 may be variable angle holes configured to receive bone fixation elements 222 therein, at any user-selected angle (relative to central axes thereof) within a permitted range of angulation. The plate 200, however, further comprises a fourth portion 224 which, when the plate 100 is in the desired position, extends over a talus 22. Thus, in addition to compression of the naviculocuneiform and tarsometatarsal joints 18, 20, the bone plate 200 also provides for compression of a talonavicular joint 24.

The second portion 208 may be substantially similar to the second portion 108 as described above in regard to the plate 100, including, for example, openings 212d, 212e and a first compression slot 214. The third portion 210 may be substantially similar to the third portion 110 of the plate 100, including, for example, openings 212f, 212g and a second compression slot 216.

The fourth portion 224, however, extends distally from the proximal end 202 to the proximal end of the first portion 206 and is sized and shaped substantially similarly to the first portion 106 of the plate 100. In particular, the fourth portion 224 has a width wider than a remaining portion of the plate 100 and includes a plurality of openings 212 extending therethrough from the first surface 218 to the second surface 220, with the openings 212 aligned along an axis transverse to a longitudinal axis L2 of the plate 200. In one exemplary embodiment, the fourth portion 224 includes two openings 212a, 212b extending therethrough. The first opening 212a extends through a portion of the fourth portion 224 closest to a lateral side of the foot while the second opening 212b extends through a portion of the fourth portion 224 closest to a medial side of the foot on the opposite side of the longitudinal axis L2 from the first opening 212a. The fourth portion 224 also includes a third compression slot 226 between the openings 212a, 212b. The third compression slot 226 is elongated along an axis substantially parallel to the longitudinal axis L2 of the plate 200 to provide for compression along this axis.

The first portion 206 extends between the fourth and second portions 224, 208—distally from the fourth portion 224 and proximally from the second portion 208. The first portion 206 in this embodiment includes a plurality of openings 212 extending therethrough from the first surface 218 to the second surface 220. In particular, the first portion 206 in this embodiment includes two openings 212—a first opening 212h extending through the first portion 206 slightly distally of a second opening 212i with the first opening 212h extending through a portion of the plate 200 on a first side of the longitudinal axis L2 and the second opening 212i extending through a portion of the plate 200 on a second side of the longitudinal axis L2 opposite the first side.

An exemplary surgical method using the plate 200 is substantially similar to the exemplary method described above in regard to the plate 100. The plate 200 is positioned along the medial column 10 with the fourth portion 224 extending along the talus 22, the first portion 206 extending along the navicular 12, the second portion 208 extending along the medial cuneiform 14 and the third portion 210 extending along the first metatarsal 16. Upon positioning the plate 200 in the desired position along the medial column, a bone fixation element is inserted into one of the openings 212. In particular, a bone fixation element 222 is inserted through the opening 212a closer to the lateral side of the patient's foot. A first compression wire or post is inserted into the other opening 212b. Second and third compression wires or posts are then inserted into the first and second compression slots 214, 216 and compression is applied to the naviculocuneiform and tarsometatarsal joints 18, 20 as described above in regard to the plate 100.

Upon compression of the naviculocuneiform and tarsometatarsal joints 18, 20, a fourth compression wire or post is inserted into the third compression slot 226. The fourth compression wire is inserted into a proximal end of the third compression slot 226 to maximize the compression of the joint. Compression forceps, or other compression devices, may use the first and fourth compression wires to apply compression to the talonavicular joint 24 in a manner similar to that described above. Once the talonavicular joint 24 has been compressed as desired, a bone fixation element 222 is inserted into one of the openings 212a, 212b of the fourth portion 224. Additional bone fixation elements 222 may then be inserted through any remaining openings 212, 216 of the bone plate 200 as desired.

Figure 7:
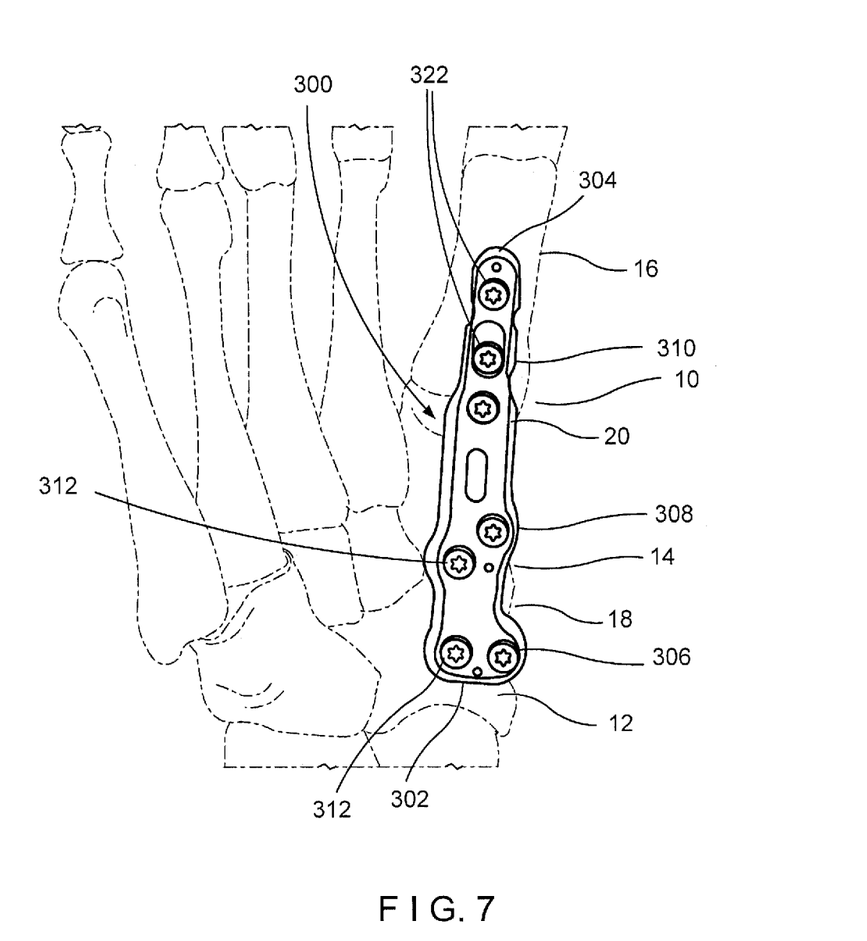
FIG. 7 shows a perspective view of a bone plate according to a third exemplary embodiment of the present invention.
Figure 8:
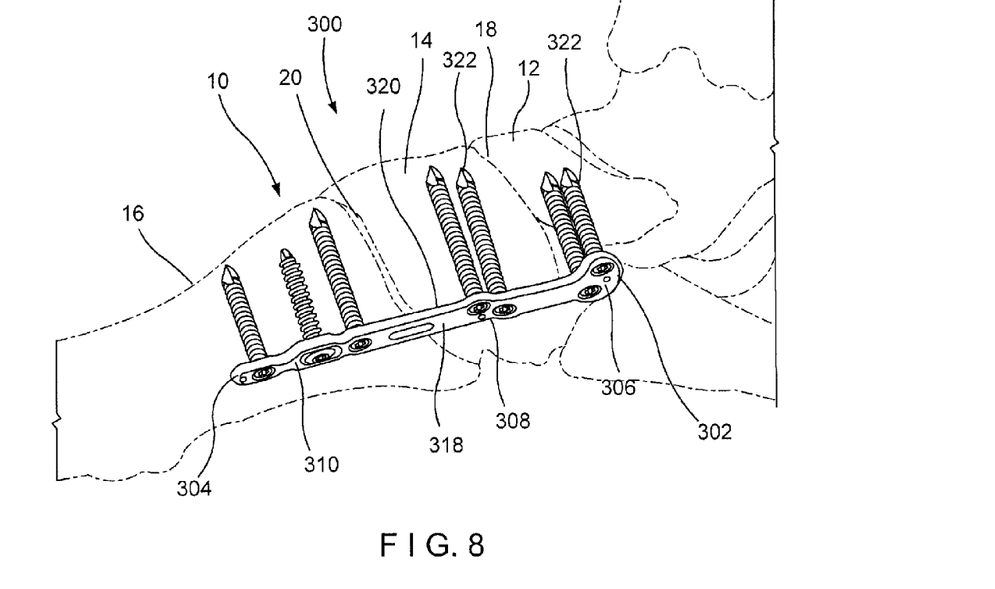
FIG. 8 shows a side view of the bone plate of FIG. 7.
Figure 9:
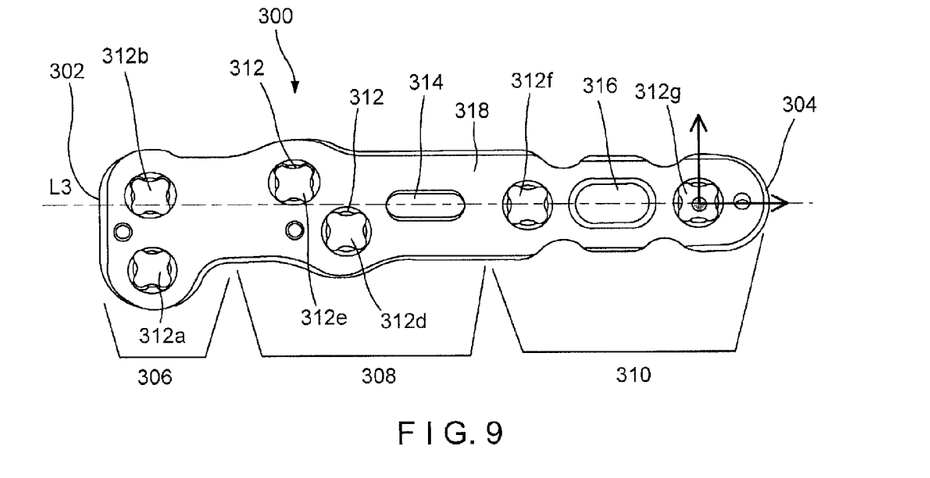
FIG. 9 shows a top plan view of the bone plate of FIG. 7.

As shown in FIGS. 7-9, a bone plate 300 according to a third exemplary embodiment of the present invention is substantially similar to the plate 200 described above except as pointed out below. The plate 300 extends along a longitudinal axis from a proximal end 302 to a distal end 304 and is configured so that, when in a desired position, a first portion 306 thereof extends over a navicular 12, a second portion 308 extends over a medial cuneiform 14 and a third portion 310 extends over a first metatarsal 16. The plate 300, however, is specifically configured for plantar application (i.e., along an underside of the foot). Similarly to the plate 100, the plate 300 includes a plurality of openings 312 extending therethrough from a first surface 318 which, when the plate 300 is in the desired position, faces away from the medial column 10, to a second surface 320 which faces the medial column 10. Any or all of the openings 312 may be variable angle holes configured to receive a bone fixation element 322 therein at any user-selected angle (relative to a central axis of the corresponding opening 312) within a permitted range of angulation.

The first portion 306 according to this embodiment is substantially similar to the first portion 106 of the plate 100, having a width larger than that of a remaining length of the plate 300. The first portion 306, however, only extends laterally away from the longitudinal axis L3 in one direction. In particular, when the plate 300 is positioned along the plantar of the medial column 10, the increased width of the first portion 306 extends laterally toward a medial side of the foot on which the plate 300 is positioned. The first portion 306 according to this embodiment includes two openings 312a, 312b, aligned along an axis transverse to the longitudinal axis of the plate 300. The opening 312a is offset from the longitudinal axis L3. The opening 312b may be offset from the longitudinal axis or located on the longitudinal axis L3.

The second portion 308 is substantially similar to the second portion 108 of plate 100, including two openings 312d, 312e and a first compression slot 314 and the third portion 310 is substantially similar to the third portion 110 of the plate 100, including two openings 312f, 312g through proximal and distal portions thereof, respectively, with a second compression slot 316 between the openings 312f and 312g. The third portion 310, however, does not extend along a curve in a plane extending through the longitudinal axis L3 of the plate 300 substantially perpendicular to a central axis of the opening 312f as with the plate 100 to more closely conform to the geometry of the plantar side of the bones.

It will be understood by those of skill in the art that a surgical method using the plate 300 is substantially similar to the exemplary method described above in regard to the plate 100. The plate 300, however, is positioned along the plantar (i.e., underside of the foot) rather than along a medial or dorsomedial side of the foot. Compression of the naviculocuneiform and tarsometatarsal joints 18, 20 is provided in the same manner as described above and the plate 300 is fixed to the medial column 10 via bone fixation elements 322, substantially as described above.

It will be apparent to those skilled in the art that various modifications may be made in the present invention, without departing from the spirit or scope of the invention. Thus, it is intended that the present invention cover modifications and variations of this invention provided that they come within the scope of the appended claims and their equivalents.

What is claimed is:

1. A medial column bone plate, comprising:
    a first portion which, when the plate is positioned along a medial column of a foot in a desired position, extends along a navicular, the first portion including at least two first variable angle holes extending therethrough, each of the first variable angle holes configured to receive a bone fixation element therethrough at a user-selected angle relative to a central axis thereof;

a second portion extending distally from the first portion so that when the plate is in the desired position, the second portion extends along a medial cuneiform, the second portion including at least one second variable angle hole configured to receive a bone fixation element therein at a user-selected angle relative to a central axis thereof and a first compression slot extending therethrough; and a third portion extending distally from the second portion so that the third portion extends along a first metatarsal of the medial column in the desired position, the third portion including a third variable angle hole configured to receive a bone fixation element therein at a user-selected angle relative to a central axis thereof and a second compression slot extending therethrough, wherein the third portion extends along a curve in a plane extending through a longitudinal axis of the plate and substantially perpendicular to the central axis of the third variable angle hole, the curve of the third portion substantially corresponding to a natural curvature of the medial column.

2. The plate of claim 1, wherein a distance between longitudinal edges of the first portion is larger than a distance between longitudinal edges of a remaining length of the plate.

3. The plate of claim 1, wherein the first portion includes three variable angle holes, each of the holes aligned along an axis extending substantially perpendicular to a longitudinal axis of the plate.

4. The plate of claim 1, wherein the second portion includes two second variable angle holes.

5. The plate of claim 4, wherein the two second variable angle holes are offset from one another along a length of the plate and from a longitudinal axis of the plate.

6. The plate of claim 1, wherein the third portion includes a first third variable angle hole through a proximal portion thereof and a second third variable angle hole through a distal portion thereof.

7. A medial column bone plate, comprising:
a first portion which, when the plate is positioned along a medial column of a foot in a desired position, extends along a navicular, the first portion including at least two first variable angle holes extending therethrough, each of the first variable angle holes configured to receive a bone fixation element therethrough at a user-selected angle relative to a central axis thereof;

a second portion extending distally from the first portion so that when the plate is in the desired position, the second portion extends along a medial cuneiform, the second portion including at least one second variable angle hole configured to receive a bone fixation element therein at a user-selected angle relative to a central axis thereof and a first compression slot extending therethrough;

a third portion extending distally from the second portion so that the third portion extends along a first metatarsal of the medial column in the desired position, the third portion including a third variable angle hole configured to receive a bone fixation element therein at a user-selected angle relative to a central axis thereof and a second compression slot extending therethrough; and a fourth portion extending proximally from the first portion so that, when the plate is in the desired position along the medial column, the fourth portion extends along a talus of the medial column, the fourth portion including two fourth variable angle holes each of which are configured to receive a bone fixation element therethrough at a user-selected angle relative to a central axis thereof.

8. The plate of claim 7, wherein a distance between longitudinal edges of the fourth portion is larger than a distance between longitudinal edges of a remaining length of the plate.

9. The plate of claim 7, wherein the fourth portion comprises a third compression slot between the two fourth variable angle holes.

10. The plate of claim 1, wherein the plate is contoured to be positioned along the medial column from a dorsomedial side of the foot.

11. The plate of claim 1, wherein the plate is contoured to be positioned along the medial column from a plantar side of the foot.

12. The plate of claim 1, wherein the first portion extends laterally away from a longitudinal axis of the plate toward a lateral side of the foot when the plate is positioned in the desired position along the medial column.

13. A method for treating a medial column of a foot, comprising:
positioning a plate along a medial column of a bone such that a first portion of the plate extends along a navicular, a second portion extends along a medial cuneiform and a third portion extends along a first metatarsal;

inserting a bone fixation element through a first opening extending through the first portion to fix the first portion to the navicular;

inserting a first compression element through a second opening extending through the first portion of the plate;

inserting a second compression element through a distal end of a first compression slot extending through the second portion of the plate;

compressing a naviculocuneiform joint between the navicular and medial cuneiform by drawing the first and second compression elements toward one another; and fixing the second portion of the plate to the medial cuneiform by inserting a bone fixation element through an opening extending through the second portion of the plate, wherein the third portion extends along a curve in a plane extending through a longitudinal axis of the plate and substantially perpendicular to an opening extending through the third portion, the curve substantially corresponding to a natural curvature of the medial column.

14. The method of claim 13, further comprising:
removing the second compression element and inserting a third compression element into a distal end of a second compression slot extending through the third portion of the plate;

compressing a tarsometatarsal joint between the medial cuneiform and the first metatarsal by drawing the first and third compression elements toward one another; and fixing the third portion to the first metatarsal by inserting a bone fixation element through the opening extending through the third portion.

15. The method of claim 14, further comprising:
removing the third compression element and inserting a fourth compression element into a proximal end of a third compression slot extending through a fourth portion of the plate extending proximally from the first portion to extend over a talus of the medial column;

compressing a talonavicular joint between the talus and the navicular by drawing the first and fourth compression elements toward one another; and fixing the fourth portion to the talus by inserting a bone fixation element through an opening extending through the fourth portion.

16. The method of claim 15, wherein the openings extending through the first, second, third and fourth portions of the plate are variable angle holes, each of which is configured to receive a bone fixation element therein at a user-selected angle relative to a central axis thereof within a permitted range of angulation.

17. The method of claim 13, wherein the plate is positioned along a dorsomedial side of the medial column of the foot.

18. The method of claim 13, wherein the plate is positioned along a plantar side of the medial column of the foot.

* * * * *